United States Patent [19]

Hörnell

[11] 4,240,709
[45] Dec. 23, 1980

[54] MULTIPLE LAYER PROTECTIVE GLASS, PARTICULARLY A PROTECTIVE GLASS FOR A WELDING SHIELD

[75] Inventor: Ake Hörnell, Gagnef, Sweden

[73] Assignee: ESAB Aktiebolag, Gothenburg, Sweden

[21] Appl. No.: 33,011

[22] Filed: Apr. 24, 1979

[30] Foreign Application Priority Data

Apr. 24, 1978 [SE] Sweden ............................. 7804630

[51] Int. Cl.³ ............................................. G02F 1/133
[52] U.S. Cl. ................................. 350/335; 350/331 R; 350/334
[58] Field of Search ................... 350/335, 334, 331 R, 350/341; 2/8

[56] References Cited

U.S. PATENT DOCUMENTS

| | | | |
|---|---|---|---|
| 3,873,804 | 3/1975 | Gordon | 350/331 R X |
| 3,890,628 | 6/1975 | Gurtler | 350/335 X |
| 3,947,185 | 3/1976 | Malzawa | 350/334 |
| 3,977,767 | 8/1976 | O'Ruma et al. | 350/341 |
| 4,039,254 | 8/1977 | Harsch | 350/335 |

Primary Examiner—Edward S. Bauer
Attorney, Agent, or Firm—Morgan, Finnegan, Pine, Foley & Lee

[57] ABSTRACT

A multiple layer protective glass, particularly a protective glass for a welding shield, for damping the light transmission, the layers of which are in turn comprised at least of a first polarizer, a first electrooptical cell, a second polarizer, a second electrooptical cell and a third polarizer, the electrooptical cells consisting of liquid crystals enclosed between transparent parallel plates coated with electrically conducting layers, said crystals being arranged in their non-excited condition to form a helically twisted structure for rotating the plane of polarization of the passing polarized light. The planes of polarization of the first and the second polarizer (2,4) are at right angles to each other. The planes of polarization of the second and the third polarizer (4,6) enclose an angle which is between 0° and 60°. The angle of rotation of the helical structure formed by the liquid crystals in the second electrooptical cell (5) is between 90° and 30° and the said angle and the angle of rotation are complementary angles. Means (13) are provided for exciting the two electrooptical cells (3,5) in opposite modes by the application of a voltage between the conducting layers (10a,11a; 10b,11b) of the electrooptical cell.

9 Claims, 5 Drawing Figures

MULTIPLE LAYER PROTECTIVE GLASS, PARTICULARLY A PROTECTIVE GLASS FOR A WELDING SHIELD

The invention refers to a multiple layer protective glass, particularly a protective glass for a welding shield, for damping the light transmission, the layers of which are in turn comprised at least of a first polarizer, a first electrooptical cell, a second polarizer, a second electrooptical cell and a third polarizer, the electrooptical cells consisting of liquid crystals enclosed between transparent parallel plates coated with electrically conducting layers, said crystals being arranged in their non-excited condition to form a helically twisted structure for rotating the plane of polarization of the passing polarized light.

The liquid crystal enclosed between the plates consists of a substance having a nematic phase and positive dielectric anisotrophy. The dielectric anisotrophy causes the molecules, in the case of excitation through a sufficiently strong electric field, to place themselves in the direction of the field lines. When a field is applied to the crystal between the parallel plates this field is essentially homogenous and all molecules with the exception of the boundary layer adhering to the plates will place themselves parallelly and because of the configuration of the field at right angles to the plates. When the molecules occupy this position the passing light will not be appreciably influenced by the liquid crystal In the nonexcited condition the structure of the crystal is determined by the orientation of the molecules in the two boundary layers adhering to the plates. If the orientation of the molecules in one boundary layer is not parallel to the orientation of the molecules in the other boundary layer, the molecules in the liquid crystal will form a helical structure. When polarized light passes through such a crystal the plane of polarization of the light follows substantially the rotation of the helical structure.

The various optical properties of the liquid crystals in the excited and the non-excited conditions in combination with polarizers have been utilized in protective glasses for damping the light, e.g. the arc light in the case of welding operations. Such a protective glass consists in its simplest form of three layers, namely a liquid crystal, a front and a back polarizer. In one embodiment the planes of polarization of the polarizers are parallel. The liquid crystal has a helical structure which rotates the plane of polarization of the light through an angle of 90°. If the liquid crystal is not excited the light polarized in the front polarizer cannot, after the rotation in the liquid crystal, pass through the back polarizer. On the other hand, if the crystal is excited the light is passed through the crystal without rotation and the back polarizer forms no barrier to the light. The excitation of the crystal is preferably controlled by means of photo-sensors which sense the intensity of the incident light and converts the crystal into the non-excited condition when the light becomes too strong. The transition from the excited into the non-excited condition takes some tenth of a second. During this time the welder is subjected to a short but intense blinding which is not only troublesome but can also be deleterious to his eyesight. Protective glasses of this type besides do not damp the light sufficiently on account of the inperfections of the polarizers and the liquid crystal.

In another embodiment of such a protective glass the planes of polarization of the polarizers are at right angles to each other. The liquid crystal has a helical structure for a 90° rotation of the plane of polarization of the light. If the crystal is non-excited the light can pass through the protective glass almost without hindrance. If the crystal is excited the plane of polarization of the light is not rotated and the light polarized in the first polarizer is damped in passing through the second polarizer. The transition from non-excited into excited condition takes place much more rapidly than the transition in the reverse direction. A protective glass of this kind is therefore better suited with regard to the shorter blinding time during the change-over time which lasts some hundredths of a second. Also a protective glass of this construction does not damp the light sufficiently. Such a protective glass also has the disadvantage that its protective effect ceases with the disappearance of the exciting voltage.

In the U.S. Pat. No. 4,039,254 there is described a multiple layer protective glass which consists of two protective glasses disposed behind each other, the polarizers of which have parallel planes of polarisation. Thereby better damping is achieved. The transmission of the protective glass with non-excited crystals is less than 0.01%. The transition from excited condition into non-excited condition takes too long time, however, and the welder is not protected efficiently enough against blinding during this change-over time.

The object of the present invention is to provide a multiple layer protective glass having an efficient blinding protection and is characterized by the fact that the planes of polarization of the first and the second polarizer are at right angles to each other and the planes of polarization of the second and the third polarizer enclose an angle which is between 0° and 60°, the angle of rotation of the helical structure formed by the liquid crystals in the second electrooptical cell being between 90° and 30° and the said angle and the angle of rotation being complementary angles, and means for exciting the two electrooptical cells in opposite modes by the application of a voltage between the conducting layers of the electrooptical cell.

According to a preferred embodiment of the invention the layer of the liquid crystal in the first electrooptical cell is not more than 0.008 mm, preferably not more than 0.003 mm thick. Thereby, at the excitation of the first cell change-over times are attained which are substantially shorter than about 0.02 seconds. During such a short time the light from a welding arc is not perceived as troublesome.

To attain the best contrast in the protective glass portion formed by the first and the second polarizer and the first electrooptical cell the angle of rotation of the helical structure of the non-excited liquid crystal should be 90°. By contrast is here meant the ratio of the light transmission through the protective glass unit with non-excited and excited crystal.

In the non-excited liquid crystal the passing polarized light is depolarized to a certain extent. The depolarization increases with decrease of the pitch angle of the helical structure which is a function of the thickness of the crystal and the angle of rotation of the structure. The thinner the crystal and/or the more rotated the structure, the less the plane of polarization of the passing light will follow the helical structure. The closeness of following is, inter alia, dependent on the wavelength of the light. The polarized light portions are damped more or less than the non-depolarized portions in the polarizer disposed behind the cell, dependent on the rotation of its plane of polarization in relation to the plane of polarization of the non-depolarized light portion.

The multiple layer glass according to the invention is "closed", i.e. the passing light is damped very strongly when the first electrooptical cell is excited and the second is non-excited. The light polarized by the first polarizer passes uninfluenced through the first excited cell and is damped efficiently by the second polarizer, the plane of polarization of which is at right angles to the plane of polarization of the first polarizer. Thanks to the excitation of the first cell the change-over time is short. Yet, the damping of the light is not sufficient if, for example, a welding arc has to be observed for a long time. A further damping of the residual light which passes through the second polarizer and which substantially is polarized in a plane parallel to the plane of polarization of the second polarizer takes place through the third polarizer.

The depolarization of the residual light in the non-excited second cell is influenced by selecting the angle of rotation which has to be between 90° and 30°. It is besides advantageous that the crystal in the second cell is slightly thicker than in the first. According to an advantageous construction the second crystal is at least 0.002 mm thicker than the first crystal.

To get the lowest possible transmission in a non-excited condition of the second cell the plane of polarization of the third polarizator must be adapted to the angle of rotation in the helical structure of the cell. The plane of polarization of the third polarizer has to be so rotated in relation to the plane of polarization of the second polarizer that the plane of polarization of the residual light emerging from the second cell is substantially at right angles to the plane of polarization of the third polarizer. The angle of rotation in the helical structure of the second cell and the angle between the planes of polarization of the second and the third polarizer must therefore be complementary, i.e. the sum has to be 90°. For reasons of manufacturing technique, however, an exact adjustment of these two angles is often difficult to realize. Minor deviations from the sum of 90° have not detrimental influence on the damping. Within the scope of the present invention, by complementary angles is here meant such angles whose sum is between 80° and 100°.

The multiple layer glass is "open", i.e. the main portion of the incident light passes through when the first cell is non-excited and the other is excited. Since the angle of rotation of the first cell in the helical crystal structure is large and the cell is thin there will in this thin cell occur an appreciable depolarization which results in a certain but not troublesome damping of the light through the second polarizer. Further damping of the passing light then arises in the third polarizer after the unimpeded passage of the light through the excited second cell when the plane of polarization of the third polarizer is not parallel to the plane of polarization of the second polarizer, which is true in the case of using cells having a helical crystal structure the angle of rotation of which is less than 90°. The angle of rotation in the second cell should not be less than 30° since the damping through the third polarizer in the case of an "open" protective glass will be too great.

The transmission reduced through the depolarization in the first cell and the possible special damping through the third polarizer when the protective glass is "open" is nevertheless acceptable and affects the possibility of observation through the "open" protective glass only insignificantly. It is a question of suitability to be decided upon from case to case whether the transmission with "open" protective glass has to be increased at the expense of less damping with "closed" protective glass.

Further advantages of the present invention are explained in the following specification in connection with the attached drawings which show an example of execution of the invention.

Figure 1:
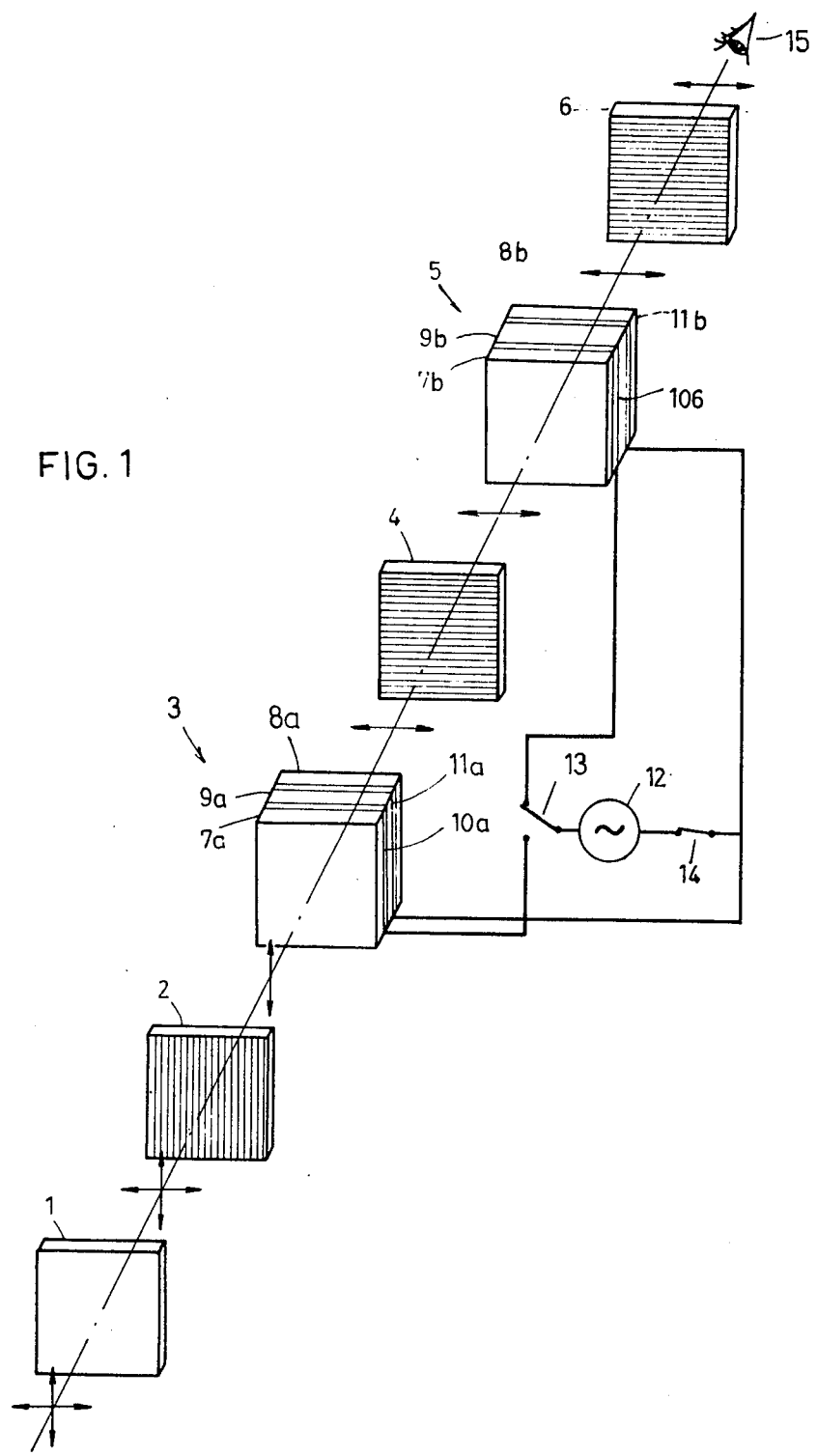
FIG. 1 shows diagrammatically a multiple layer glass having electrooptical cells in a certain condition of excitation.

The multiple layer glass consists of a first polarization filter 2 for the transmission of light waves with only vertical plane of polarization, a first electrooptical cell 3, a second polarization filter 4 for the passage of light waves with only horizontal plane of polarization, a second electrooptical cell 5 and a third polarization filter 6 for the transmission of light waves with only horizontal plane of polarization.

The capability of the polarization filter of polarizing light is retricted to a certain range of wavelengths. The infra-red and the ultra-violet light which are both essentially more injurious to health than the visible light are polarized only to a limited extent, and the protective glass is therefore provided with a special filter 1 for this light.

Each of the two electrooptical cells is provided with a liquid crystal 9a, 9b mounted between plane-parallel glass plates 7a, 8a; 7b, 8b. The glass plates are coated on the side facing the crystal with an electrically conducting layer 10a, 11a; 10b, 11b. The conducting layers are very thin and are applied in such a way that the crystal molecules in the boundary layer facing the conducting layer get a fixed orientation. The orientation in the layer 10a and 10b, respectively, shall here be substantially at right angles to the orientation in the layer 11a and 11b, respectively. The layers are connected to an oscillator 12 in series with a welding light operated switch 13. The oscillator 12 generates square wave pulses at a frequency of about 150 Hz alternately to layers 7b and 8b. This alternate feeding of layers 7b and 8b is known per se and will improve the efficiency and the life time of the cell. Cell 5 is said to be excited when fed in this manner from oscillator 12. When cell 5 is excited cell 3 is non-excited and vice versa. In other words cells 3 and 5 operate in opposite modes. Cell 3 in FIG. 1 will be excited when switch 13 by welding light is activated to the position shown in FIG. 2. With a switch 14 the circuit is closed when the protective glass is used. The switch 14 is normally open but is here shown in its operating position.

The liquid crystal 9a in the electrooptical cell 3 is about 0.003 mm thick. Its change-over time at the excitation is less than 0.01 second. The liquid crystal 9b in the electrooptical cell 5 is about 0.01 mm thick. Its change-over time is longer than that of the crystal 9a and amounts to about 0.1 seconds.

In FIG. 1, owing to the position of the switch 13 the crystal 3 is non-excited and the crystal 5 excited. The light incident from the left in the figure first passes through the filter 1 and is polarized in the polarization filter 2. Only light waves belonging to the vertical plane are allowed to pass through by the filter 2. In the first non-excited electrooptical cell 3 the plane of polarization is rotated 90° and therefore the light passes unimpedely through the second polarization filter 4. The second excited electrooptical cell 5 allows the light to pass without rotation and therefore the light can also pass through the third polarization filter 6 and thus reach an observer 15. The position of the plane of polarization of the light is shown diagrammatically in FIGS. 1 and 2 by arrows.

Figure 2:
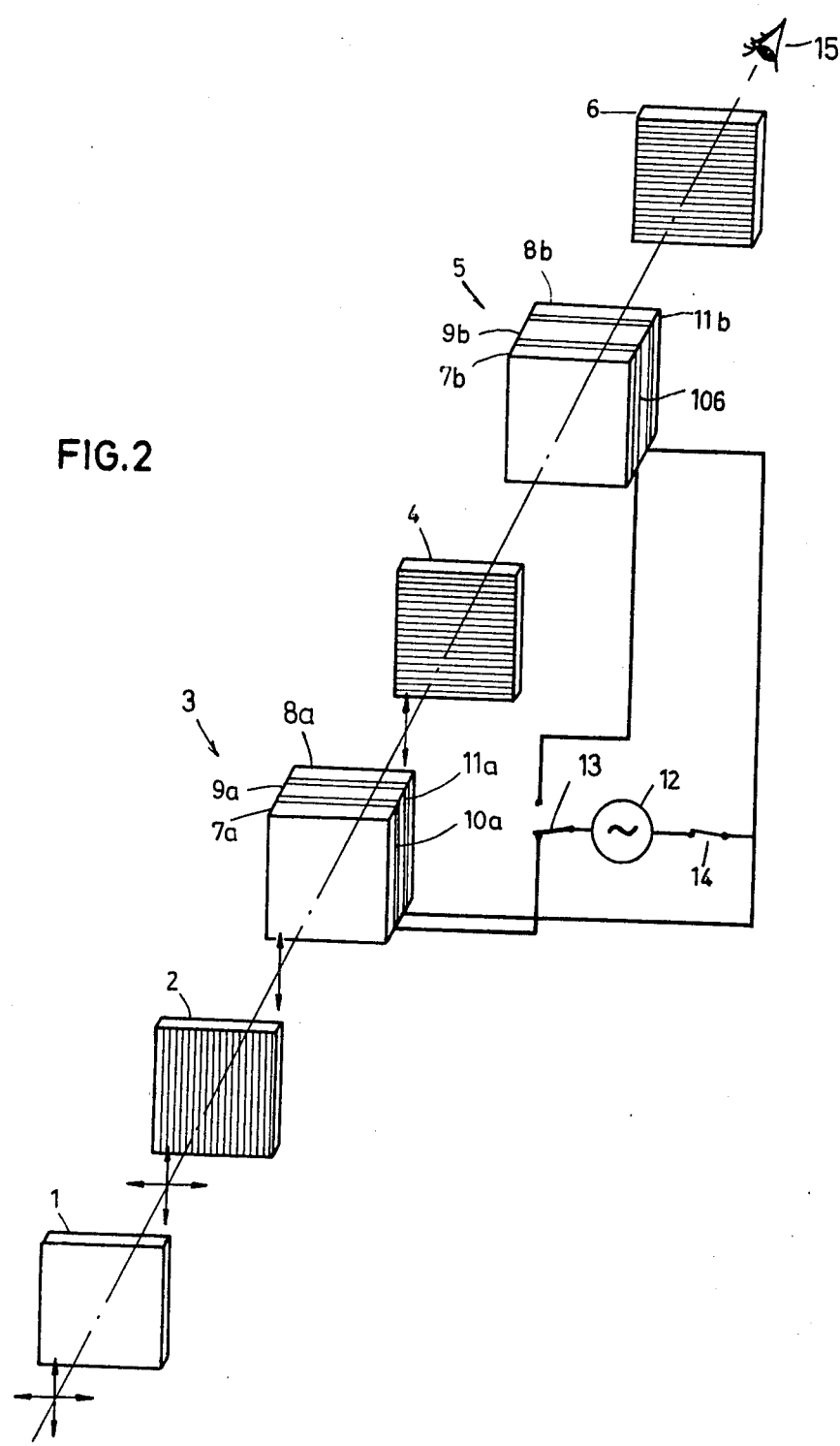
FIG. 2 shows the protective glass with the electrooptic cells in another condition of excitation.

In FIG. 2 the switch 13 is in its second position. The crystal 3 is excited and the crystal 5 non-excited. The polarized light which has left the polarization filter 2 passes through the crystal 3 without rotation. The polarization filter 4 now forms a stop for further passage and therefore light does not reach the observer 15. Owing to the depolarizing action of the liquid crystal some light with a horizontal plane of polarization will nevertheless pass through the filter 4. Its plane of polarization will be rotated in the liquid crystal 9b and therefore cannot pass through the third polarization filter 6.

In FIG. 3a a protective glass unit 17 is provided with the elements shown in FIG. 1 and FIG. 2 and besides with a scratch protective glass 18. The glass elements are cemented together and the glass surfaces are, if considered advisable, anti-reflex coated. The conducting layers 10a, 11a; 10b, 11b are connected to one output each of exclusive-OR-gates 19, 20, 21, 22 which with one of their two inputs are connected to the output of the oscillator 12 whose frequency is set to about 150 Hz. A frequency between 100 and 400 Hz is suitable. Higher frequencies result in greater losses and lower frequencies cause flicker.

The output of the oscillator 12 is alternately connected to the two potentials of a battery 24 when switch 14 is closed. The other input of the exclusive-OR-gate 19 is connected with one—here, for example, the positive—potential of the battery. The other input of the exclusive-OR-gate 22 is connected with the other potential—here, for example, the zero potential—of the battery 24. The battery 24 also supplies a phototransistor 26 in series with a resistor 27. The emitter of the transistor is connected with the other inputs of the exclusive-OR-gates 20, 21. Units 17, 29 and 30 form different structural parts. From electrical point of view units 30 and 29 form the welding light operated switch 13.

As long as the switch 14 is open both crystals 9a, 9b, are non-excited. The polarized light passes after the rotation in the crystal 9a through the filter 4 and is further rotated in the crystal 9b. Thus the light cannot pass through the filter 6 and therefore the transmission of the protective glass is always reduced when it is not used.

It is assumed that the switch 14 is closed and the incident light corresponds to normal illumination. The emitter of the phototransistor 26 is practically at the zero potential. The outputs of the exclusive-OR-gates 19, 20 at the same point of time always have differing potentials which change concurrently with the frequency of the oscillator 12. On the other hand, the outputs of the exclusive-OR-gates 21, 22 at the same point of time always have the same potential. Therefore, the crystal 9b is excited and the crystal 9a non-excited. The light passes through the protective glass as described above in connection with FIG. 1.

If the phototransistor 26 is subjected to strong lighting, e.g. from an arc, the emitter of the photo-transistor 26 receives positive potential. Thereby the outputs of the exclusive-OR-gates 19, 20 at the same points of time will always get the same potential and the outputs of the exclusive-OR-gates 21, 22 will get differing potentials. The crystal 9a is excited and the crystal 9b is transferred into non-excited condition. Thanks to the short changeover time of the thin crystal 9a at the excitation thereof the transmission of the protective glass has already been reduced to 0.1% after about 0.01 second. After about 0.1 second the helical structure of the thick crystal 9b is restored and the transmission of the protective glass is lower than 0.01%. The welder is practically not exposed to any blinding. After 0.01 second the light from the arc has already been reduced to an acceptable level, and after 0.1 second the protective glass is dark enough for a continuous control of the arc.

When the arc goes out the crystals again pass into the condition described in FIG. 1 and the light can pass through the protective glass fairly unimpededly.

Figure 3:
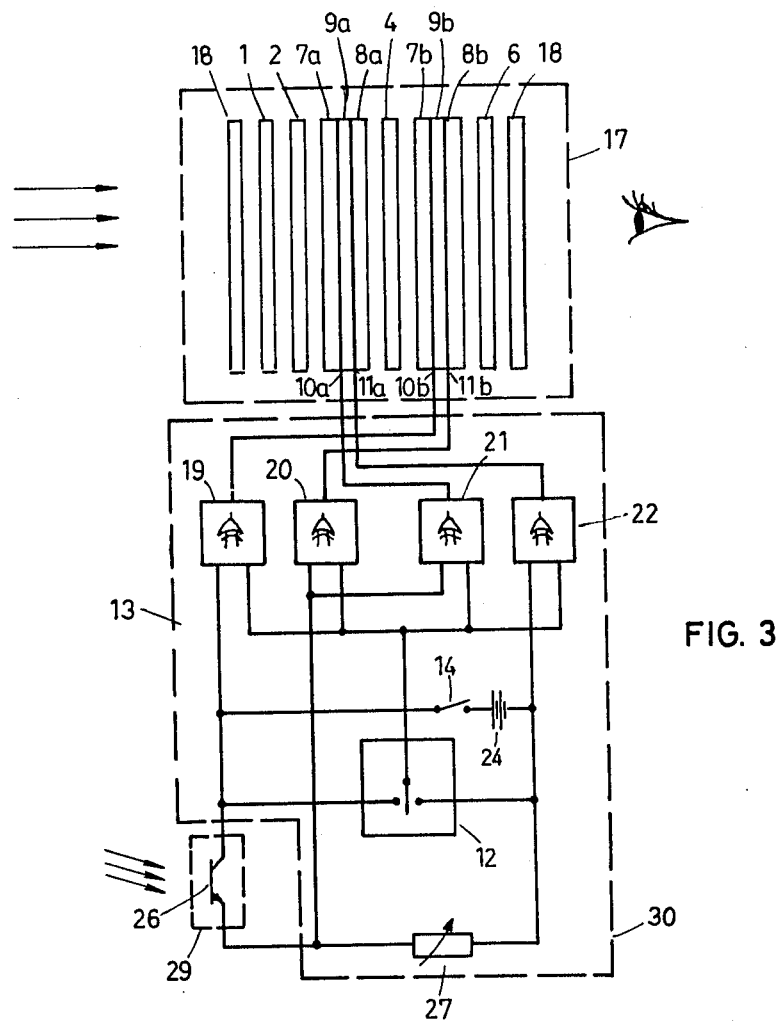
FIG. 3 shows a block diagram for controlling the light transmission of the protective glass.
Figure 4:
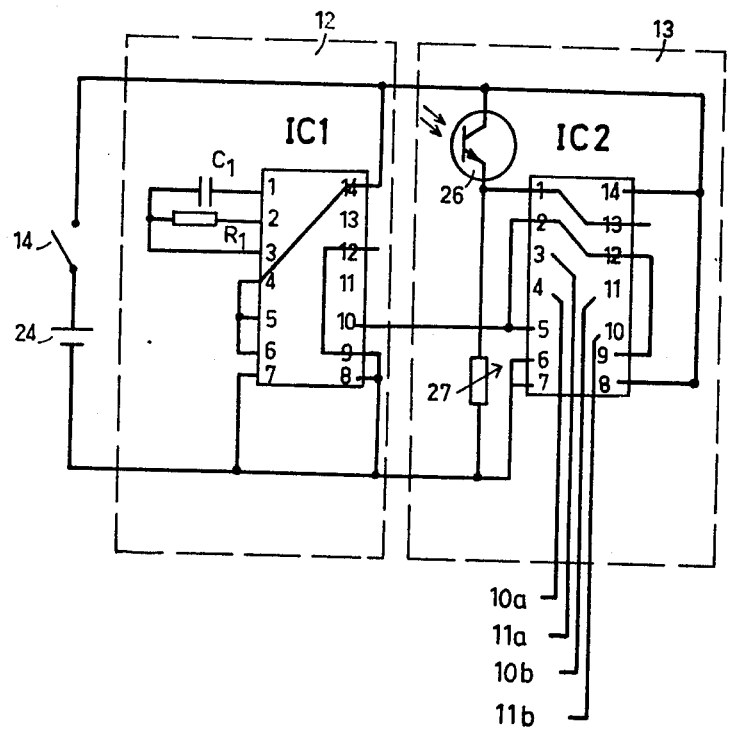
FIG. 4 shows a detailed circuit diagram of the block diagram of FIG. 3.

In FIG. 4 the control circuit of FIG. 3 is shown in detail. The following components are used:

IC1, RCA CD 4047 wired as an astable multivibrator
IC2, 4070 wired as four exclusive-OR-gates
$C_1$, abt. 10 nF
$R_1$, 100 k–500 k$\Omega$
27, 1 M$\Omega$ trim potentiometer
13, phototransistor The $R_1C_1$ combination determines the frequency of the oscillator the output of which is at pin 10 of IC1. With 27 the level is set at which the phototransistor 26 starts conducting, that is at which strength of light the protective glass shall switch from its "open" to "closed" state. Pins 3, 4, 10 and 11 of IC2 are connected to the conducting layers 10a, 11a, 10b and 11b respectively. With switch 14 closed and no welding light falling on the phototransistor its emitter is low and pins 10, 11 are high while pins 3, 4 are low. When welding light then is falling upon the phototransistor its emitter goes high, pins 10, 11 go low and pins 3, 4 go high.

Figure 5:
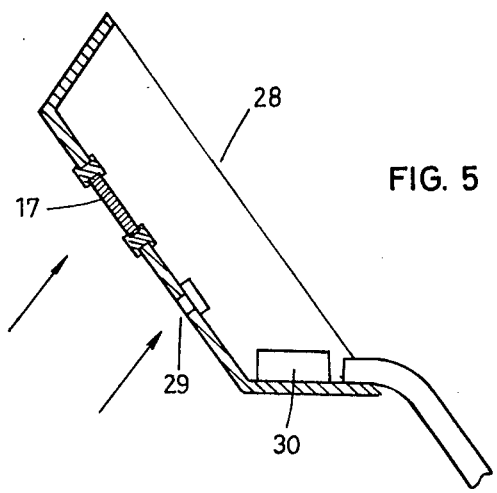
FIG. 5 shows a welding shield equipped with the protective glass.

In FIG. 5 there is shown a welding shield 28 which is provided with the protective glass unit 17. The phototransistor 26 is provided with a casing 29 which is mounted in the shield front. The control circuit 30 takes up little space and is mounted on the inside of the shield.

I claim:

1. A multiple layer protective glass, particularly a protective glass for a welding shield, for damping the light transmission, the layers of which are in turn comprised at least of a first polarizer, a first electrooptical cell, a second polarizer, a second electrooptical cell and a third polarizer, the electooptical cells consisting of liquid crystals enclosed between transparent parallel plates coated with electrically conducting layers, said crystals being arranged in their non-excited condition to form a helically twisted structure for rotating the plane of polarization of the passing polarized light, characterized by the fact that the planes of polarization of the first and the second polarizer (2, 4) are at right angles to each other, that the planes of polarization of the second and the third polarizer (4, 6) enclose an angle which is between 0° and 60°, the angle of rotation of the helical structure formed by the liquid crystals in the second electrooptical cell (5) being between 90° and 30° and the said angle and the angle of rotation being complementary angles, and means (13) for exciting the two electrooptical cells (3, 5) in opposite modes by the application of a voltage between the conducting layers (10a, 11a; 10b, 11b) of the electrooptical cell.

2. A multiple layer protective glass according to claim 1, characterized by the fact that the angle of rotation of the helical structure formed by the liquid crystals in the first electrooptical cell is 90°.

3. A multiple layer protective glass according to claim 1 or 2, characterized by the fact that the angle between the planes of polarization of the second and the third polarizer (4,6) is between 0° and 30° and the angle of rotation of the helical structure of the second electrooptical cell (5) is between 90° and 60°.

4. A multiple layer protective glass according to claims 1 or 2, characterized by the fact that a filter (1) for infra-red and/or ultra-violet radiation is provided in front of the polarizer (2) situated nearest in respect of the incident light.

5. A multiple layer protective glass according to claims 1 or 2, characterized by the fact that the layer (9a) of the liquid crystal in the first electrooptical cell (3) is not more than 0.008 mm thick.

6. A multiple layer protective glass according to claim 5, characterized by the fact that the layer (9a) of the liquid crystal in the first electrooptical cell (3) is not more than 0.003 mm thick.

7. A multiple layer protective glass according to claim 5, characterized by the fact that the layer (9b) of the liquid crystal in the second electrooptical cell (5) is thicker than in the first cell (3).

8. A multiple layer protective glass according to claim 7, characterized by the fact that the layer (9b) of the liquid crystal in the second electrooptical cell (5) is at least 0.002 mm thicker than in the first cell.

9. A multiple layer protective glass according to claims 1 or 2, which is provided with a light sensitive member for controlling the excitation of the crystals in response to the intensity of the incident light, characterized by the fact that said exciting means (13) is arranged to excite the two crystals (9a, 9b) alternately, the first crystal (9a) being excited when the light intensity exceeds a certain value.

* * * * *